(12) United States Patent
Dameron et al.

(10) Patent No.: US 9,823,177 B2
(45) Date of Patent: Nov. 21, 2017

(54) CALIBRATED PERMEATION STANDARDS

(71) Applicant: Alliance for Sustainable Energy, LLC, Golden, CO (US)

(72) Inventors: Arrelaine A. Dameron, Boulder, CO (US); Matthew O. Reese, Golden, CO (US); Michael D. Kempe, Littleton, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 310 days.

(21) Appl. No.: 14/633,423

(22) Filed: Feb. 27, 2015

(65) Prior Publication Data
US 2015/0241331 A1  Aug. 27, 2015

Related U.S. Application Data

(60) Provisional application No. 61/945,704, filed on Feb. 27, 2014.

(51) Int. Cl.
*G01N 15/08* (2006.01)
(52) U.S. Cl.
CPC ..... *G01N 15/0806* (2013.01); *G01N 15/0826* (2013.01)
(58) Field of Classification Search
CPC .. G01N 15/0826; G01N 15/082; G01N 15/08; G01N 15/088; G01N 15/0806
USPC .......................................................... 73/38
See application file for complete search history.

(56) References Cited

U.S. PATENT DOCUMENTS

| | | | |
|---|---|---|---|
| 4,036,915 A * | 7/1977 | Lucero | B01F 3/022 261/104 |
| 8,388,742 B2 | 3/2013 | Nunes | |
| 8,664,963 B2 | 3/2014 | Reese et al. | |
| 8,916,037 B1 | 12/2014 | Mayer et al. | |
| 2001/0003917 A1 | 6/2001 | Sagi et al. | |
| 2010/0192668 A1 | 8/2010 | Semersky et al. | |
| 2012/0062896 A1 | 3/2012 | Familia et al. | |
| 2013/0152671 A1 * | 6/2013 | Sinha | G01N 15/0826 73/38 |
| 2014/0070827 A1 | 3/2014 | Reese et al. | |

(Continued)

FOREIGN PATENT DOCUMENTS

| | | |
|---|---|---|
| EP | 0634575 B1 | 5/1998 |
| EP | 2273530 B1 | 3/2013 |
| EP | 2672246 A1 | 12/2013 |

OTHER PUBLICATIONS

Dameron, A., et al., "Understanding moisture ingress and packaging requirements for photovoltaic modules", Photovoltaics International, vol. 5-13_2, Aug. 9, 2010, pp. 1-6.

(Continued)

*Primary Examiner* — Helen Kwok
*Assistant Examiner* — Nashmiya Fayyaz
(74) *Attorney, Agent, or Firm* — Robert G. Pittelkow (57) ABSTRACT

A permeation standard is provided. The permeation standard may include a substrate that is impermeable to an analyte, an orifice disposed in the substrate, and a permeable material filling the orifice. The orifice and the permeable material are configured to provide a predetermined transmission rate of the analyte through the permeation standard. Also provided herein are methods for forming the permeation standard.

26 Claims, 3 Drawing Sheets

(56) References Cited

U.S. PATENT DOCUMENTS

2015/0268150 A1* 9/2015 Newkirk ............ G01N 15/0826
                                                              73/38

OTHER PUBLICATIONS

Reese, M., et al., "Quantitative calcium resistivity based method for accurate and scalable water vapor transmission rate measurement", Review of Scientific Instruments, vol. 82, Issue 8, Aug. 2011, pp. 085101-1-085101-10.
Kanninen, M., et al., "Gas Permeation in Multi-Layered Composite Pipe for High Pressure Pipelines", Plastic Pipes XV Conference, Sep. 20-22, 2010, Vancouver, British Columbia, Canada, pp. 1-6.
Calibrated Small Holes for Leak Testing and Measurement, Oxford Lasers, available at http://www.precisionpinholes.com/, last accessed Mar. 4, 2015.

* cited by examiner

CALIBRATED PERMEATION STANDARDS

CROSS-REFERENCE TO RELATED APPLICATIONS

This application claims priority under 35 U.S.C. §119 to U.S. Provisional Patent Application No. 61/945,704, filed on Feb. 27, 2014, the contents of which are hereby incorporated by reference in their entirety.

CONTRACTUAL ORIGIN

The United States Government has rights in this invention under Contract No. DE-AC36-08GO28308 between the United States Department of Energy and the Alliance for Sustainable Energy, LLC, the manager and operator of the National Renewable Energy Laboratory.

BACKGROUND OF THE INVENTION

Materials are being developed that resist moisture permeation in the range of $10^{-4}$ to $10^{-7}$ g/m²/day. These materials are particularly useful for flexible electronics and thin film applications. Calibrating these materials using a known water vapor transmission rate (WVTR) standard, however, is not possible using conventional methods. The normal limit of detection for commercially-available instruments is typically a WVTR of about $5 \times 10^{-4}$ g/m²/day, and custom instruments have lower limits of detection from about $10^{-4}$ to $10^{-7}$ g/m²/day. However, no standards currently exist that are capable of calibrating any instrument below a WVTR of approximately $10^{-3}$ g/m²/day at a suitable temperature and relative humidity.

Related art WVTR standards, as well as related art standards for other analytes, are made from free-standing films of polymers with known permeation properties. However, as discussed above, these standards cannot be used to measure a WVTR below approximately $10^{-3}$ g/m²/day. Further, barriers that utilize thin film inorganic layers cannot be used as standards. A barrier may limit the permeable surface area by masking with a metallic foil or by coating with an oxide coating. However, any oxide or inorganic thin film coating is limited by its defects, including pinholes, grain size, and cracks. Further, these layers are easily cracked or damaged. Barriers may easily be damaged by mishandling, resulting in a change of the WVTR.

Accordingly, it would be advantageous to provide a calibrated standard that is capable of measuring a WVTR below approximately $10^{-3}$ g/m²/day. Further, it would be advantageous to provide standards for other analytes, such as oxygen or helium, with suitable transmission rates based on the analyte and the application for the standard.

SUMMARY OF THE INVENTION

The following embodiments and aspects thereof are described and illustrated in conjunction with systems, tools, and methods that are meant to be exemplary and illustrative, not limiting in scope. In various embodiments, one or more of the above-described problems have been reduced or eliminated, while other embodiments are directed to other improvements.

Exemplary embodiments of the invention provide permeation standards and methods for forming the permeation standards. The permeation standards may be used to calibrate permeation measurement instruments. According to an aspect of the invention, a permeation standard includes a first substrate that is impermeable to an analyte, a first orifice disposed in the first substrate, and a first permeable material filling the first orifice. The first orifice and the first permeable material are configured to provide a predetermined transmission rate of the analyte through the permeation standard.

The predetermined transmission rate of the analyte through the permeation standard may be determined by a geometry of the first orifice and a permeability of the first permeable material to the analyte. The geometry of the first orifice may include a cross-sectional area of the first orifice and a length of the first orifice.

The analyte may be water vapor, in which case the predetermined transmission rate of the analyte through the permeation standard may be less than approximately $10^{-3}$ g/m²/day. The first orifice may have a diameter of approximately 100 nm to approximately 10 mm. The first substrate may be selected from the group consisting of a copper-containing alloy, aluminum, a steel alloy, silicon, and glass. The first permeable material may include a polymer or a composite material.

The permeation standard may include a capillary disposed in the first orifice. The capillary may be filled with an impermeable material.

The permeation standard may also include a second substrate that is impermeable to the analyte, a second orifice disposed in the second substrate, and a second permeable material filling the second orifice. The first substrate and the second substrate may be disposed to form a space such that the first orifice and the second orifice do not align, and a third permeable material may fill the space between the first substrate and the second substrate. The first, second, and third permeable materials may include the same polymer.

The permeation standard may also include a second orifice disposed in the first substrate. The first permeable material fills the second orifice.

According to another aspect of the invention, a method for making a permeation standard is provided. The method includes forming a first orifice in a first substrate that is impermeable to an analyte, selecting a first permeable material, and filling the first orifice with the first permeable material. The first orifice is formed and the first permeable material is selected to provide a predetermined transmission rate of the analyte through the permeation standard.

The predetermined transmission rate of the analyte through the permeation standard may be determined by a geometry of the first orifice and a permeability of the first permeable material to the analyte. The geometry of the first orifice may include a cross-sectional area of the first orifice and a length of the first orifice. The analyte may be water vapor, and the predetermined transmission rate of the analyte through the permeation standard may be less than approximately $10^{-3}$ g/m²/day.

The method may also include forming a second orifice in a second substrate that is impermeable to the analyte, filling the second orifice with a second permeable material, disposing the first substrate and second substrate to form a space such that the first orifice and the second orifice do not align, and filling the space between the first substrate and the second substrate with a third permeable material. The first, second, and third permeable materials may include the same polymer.

The method may also include forming a second orifice in the first substrate, and filling the second orifice with the first permeable material.

According to a further aspect of the invention, another permeation standard is provided. The permeation standard includes a substrate that is impermeable to an analyte, a capillary disposed in the substrate, and a permeable material at least partially filling the capillary. The capillary and the permeable material are configured to provide a predetermined transmission rate of the analyte through the permeation standard.

The predetermined transmission rate of the analyte through the permeation standard may be determined by a geometry of the capillary and a permeability of the permeable material to the analyte. The geometry of the capillary may include a cross-sectional area of the capillary and a length of a filled portion of the capillary. The analyte may be water vapor and the predetermined transmission rate of the analyte through the permeation standard may be less than approximately $10^{-3}$ g/m$^2$/day.

According to yet another aspect of the invention, another method of making a permeation standard is provided. The method includes inserting a capillary into an opening in a substrate that is impermeable to an analyte, sealing the capillary onto the substrate, selecting a permeable material, and at least partially filling the capillary with the permeable material. The capillary and the permeable material are selected to provide a predetermined transmission rate of the analyte through the permeation standard.

The sealing may be performed by soldering, welding, forming a glass-glass seal with fits, or forming a metal-glass seal. The predetermined transmission rate of the analyte through the permeation standard may be determined by a length of a filled portion of the capillary, a cross-sectional area of the capillary, and a permeability of the permeable material to the analyte.

Other objects, advantages, and novel features of the present invention will become apparent from the following detailed description of the invention when considered in conjunction with the accompanying drawings.

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION OF EXEMPLARY EMBODIMENTS

Exemplary embodiments of the present invention include permeation standards, such as WVTR standards, having impermeable substrates with at least one calibrated orifice that is filled with a material of known permeability. The substrate may be impermeable to an analyte to the limits of the testing instrumentation. The geometry, number, and filler material of the orifice(s) in the substrate may be adjusted to determine the transmission rate of the analyte through the permeation standard. For example, the cross-sectional area of each orifice, the length of each orifice, and the permeability of the material filling each orifice to the analyte may be adjusted to select the analyte transmission rate. Alternatively, a capillary that is at least partially filled with a permeable material may be embedded into the impermeable substrate. The length of the filled portion of the capillary, the inner diameter of the capillary, and the permeability of the material filling the capillary to the analyte may be adjusted to select the analyte transmission rate.

(I) Permeation Standards

Permeation generally occurs by a three-step process. The analyte (e.g., water vapor, oxygen, carbon dioxide, hydrogen, hydrocarbon, or another gas) is absorbed into the surface of a permeable material. Then the analyte diffuses through the permeable material and outgases from the other side. A permeation standard has a unique transmission rate for a particular analyte under specified testing conditions, such as temperature and relative humidity, so that the detection equipment may be calibrated for accurate sample analysis.

Figure 1A:
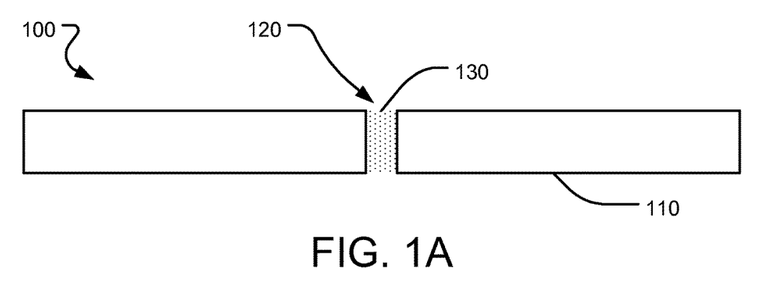
FIG. 1A shows a cross section of a permeation standard having a substrate with an orifice filled with a permeable material.
Figure 1B:
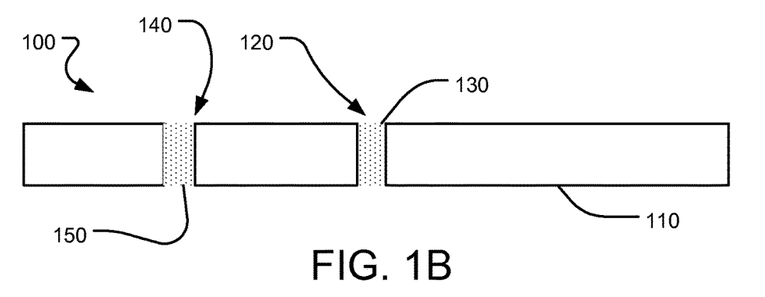
FIG. 1B shows a cross section of another permeation standard having a substrate with two orifices filled with a permeable material.
Figure 1C:
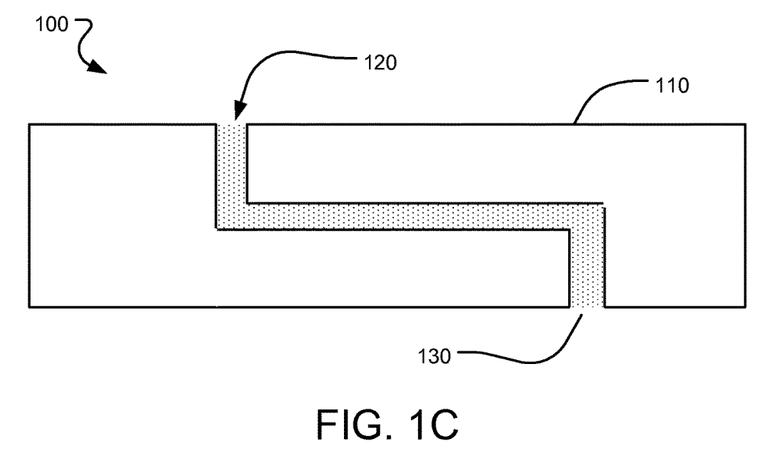
FIG. 1C shows a cross section of another permeation standard having a substrate with an orifice having a maze shape and filled with a permeable material.
Figure 1D:
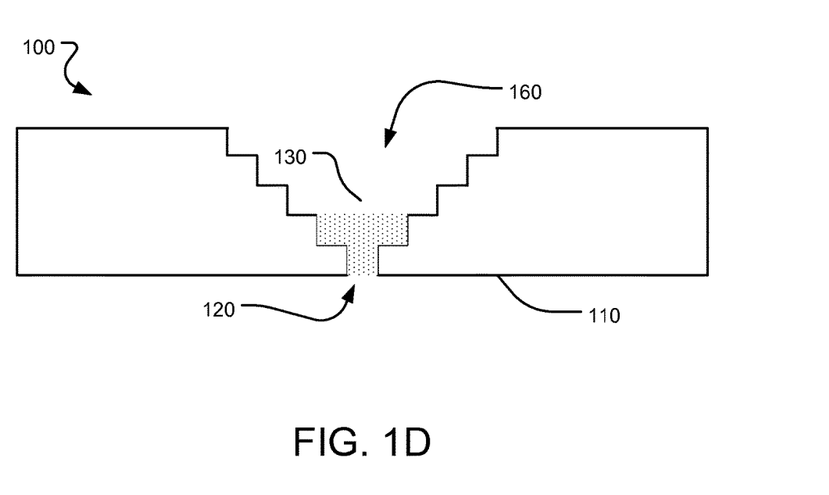
FIG. 1D shows a cross section of another permeation standard having a substrate with an opening that includes an orifice filled with a permeable material.
Figure 2A:
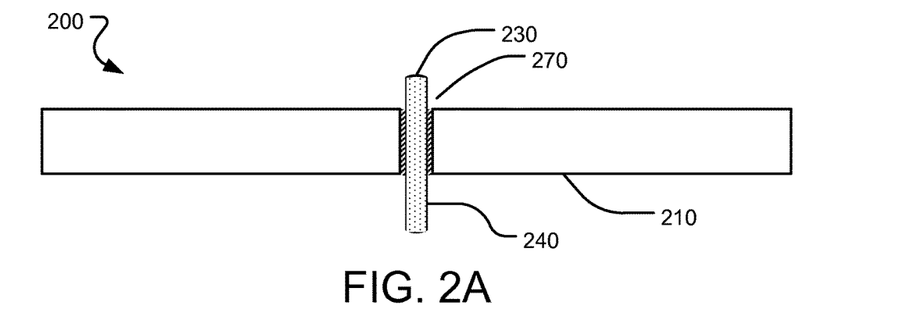
FIG. 2A shows a cross section of another permeation standard having a substrate into which a capillary filled with a permeable material is inserted.
Figure 2B:
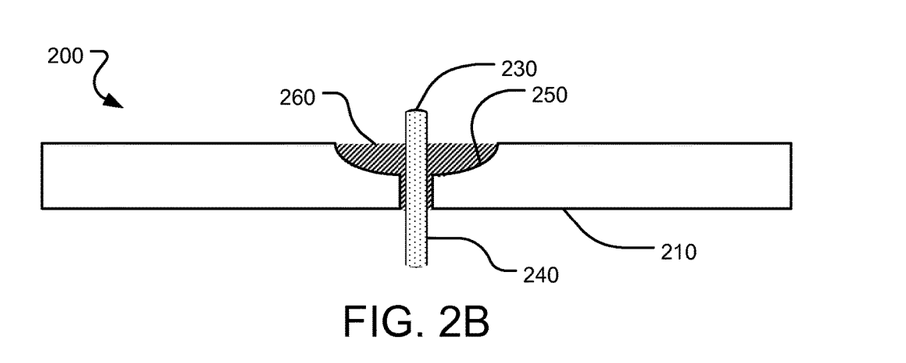
FIG. 2B shows a cross section of another permeation standard having a substrate into which a capillary filled with a permeable material is inserted, in which the substrate has a wider opening near its top surface to accommodate an anchor for sealing the capillary into the substrate.
Figure 2C:
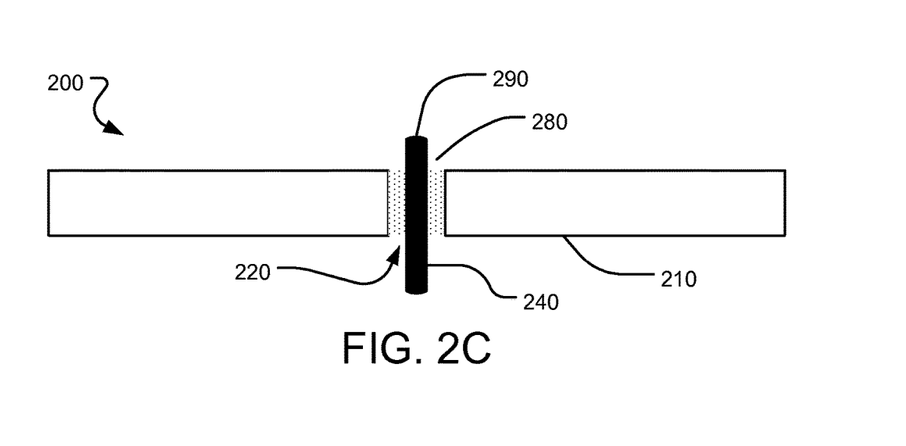
FIG. 2C shows a cross section of another permeation standard having a substrate with an orifice, filled with a permeable material, into which a capillary filled with an impermeable material is inserted.
Figure 3:
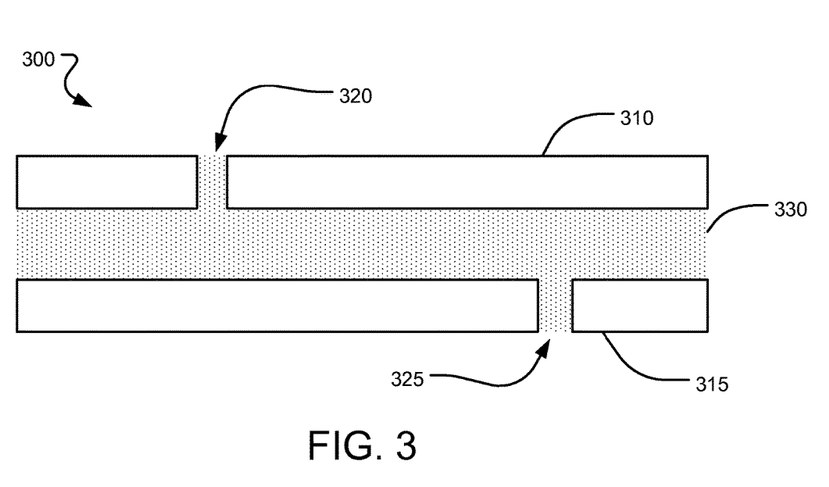
FIG. 3 shows a cross section of another permeation standard having two substrates, each of which includes an orifice filled with a permeable material, and a permeable material between the substrates.

FIGS. 1-3 show exemplary embodiments of permeation standards according to aspects of the present invention. Referring to FIG. 1A, a permeation standard 100 has an orifice 120 formed in an impermeable substrate 110. The orifice 120 is filled with a permeable material 130. Although only a single orifice 120 is shown in FIG. 1A, the permeation standard 100 may include any suitable number of orifices. For example, as shown in FIG. 1B, the substrate 110 may include a second orifice 140 that is filled with a permeable material 150. The orifices 120 and 140 may have the same geometry or different geometries. Further, the permeable material 130 may be the same as the permeable material 150, or may be different from the permeable material 150.

The permeation standard and its orifice(s) may have any suitable geometry. For example, as shown in FIG. 1C, a permeation standard 100 has an orifice 120 formed in an impermeable substrate 110 and filled with a permeable material 130. In this example, the orifice 120 has a geometry that forms a maze-shaped channel from the top of the impermeable substrate 110 to the bottom of the impermeable substrate 110. However, the orifice 120 may have any appropriate shape, as long as it provides a path for the analyte to traverse through the permeation standard 100. For example, the orifice 120 may be formed as a long spiral in any dimension with a narrow cross-section (not shown), in order to increase the length of permeable material through which the analyte must travel.

Further, the orifice 120 may be a portion of a larger opening within the impermeable substrate 110. For example, as shown in FIG. 1D, an opening 160 with a complicated shape, such as a stepwise pattern, may be formed in the impermeable substrate 110. In this case, the orifice 120 is defined as the portion of the opening 160 that is filled with a permeable material 130. The entire opening 160 need not be filled with the permeable material 130.

In other embodiments, a capillary may be inserted into the substrate. For example, FIGS. 2A and 2B show a permeation standard 200 that has a capillary 240 embedded in an impermeable substrate 210. The capillary 240 may be at least partially filled with a permeable material 230. As shown in FIG. 2A, the capillary 240 may be bonded to the substrate 210 via a seal 270, which may be made of an impermeable material. Alternatively, the capillary 240 may be bonded directly to the substrate 210 (not shown). Further, as shown in FIG. 2B, a wider opening 250 may be formed near the top surface of the substrate 210 to accommodate an anchor 260 for sealing the capillary 240 into the substrate 210. The anchor 260 may be made of an impermeable material.

In another embodiment, as shown in FIG. 2C, a capillary 240 that is filled with an impermeable material 290 may be inserted into an orifice 220 that is filled with a permeable material 280, in order to reduce the effective cross-sectional area of the permeable material 280 filling the orifice 220. The impermeable material 290 may be made from the same material as the capillary 240 itself, such that the impermeable material 290 and the capillary 240 form a solid rod, or the impermeable material 290 may be made from a different material. The impermeable material 290 may be a solid material, or may include particles and/or spheres. In another embodiment, the capillary 240 could be replaced by an impermeable material 290, such as particles and/or spheres. The capillary 240 and/or equivalent material(s) can have any appropriate shape, ranging from a solid cylindrical rod to a worm shape with holes.

In still other embodiments, such as shown in FIG. 3, a permeation standard 300 may include a first substrate 310 with a first orifice 320, and a second substrate 315 with a second orifice 325. A permeable material 330 may fill the space between the first and second substrates 310, 315, and may also fill the first and second orifices 320, 325. As shown in FIG. 3, the first and second orifices 320, 325 may be staggered such that they are not aligned with each other. The sides of the permeation standard 300 may be sealed in an impermeable manner (not shown), such that the analyte cannot leak out from the sides of the permeation standard 300, and instead is only able to enter and exit the permeation standard 300 through the first and second orifices 320, 325. For example, the analyte may enter the permeation standard 300 through the first orifice 320 and exit the permeation standard 300 through the second orifice 325, or vice versa.

The transmission rate of the standard depends on which analyte is selected for analysis. The analyte may include a gas, such as oxygen ($O_2$), carbon dioxide ($CO_2$), water vapor ($H_2O$), hydrogen ($H_2$), or a hydrocarbon gas (e.g., methane, ethane, propane, or butane). As such, the permeation standards may be used to calibrate oxygen permeation (OTR) instruments, water vapor permeation instruments (WVTR), and carbon dioxide permeation ($CO_2$ TR) instruments, and the like, depending on the analyte of interest.

(a) Impermeable Substrate

"Impermeable" as used herein refers to a material that is substantially resistant to the analyte of interest traversing the thickness dimension of the material. For example, when the analyte is water vapor, the substrate substantially blocks the water vapor from traversing from one side of the substrate to the other side of the substrate via absorption, diffusion, and desorption/outgassing.

Generally, the impermeable substrate should be resistant to corrosion by the analyte or the testing conditions. In exemplary embodiments, the impermeable substrate may include metal, alloy, glass, semiconductor, or ceramic materials. An "alloy" is a solid solution including at least one metal and at least one other metal, semimetal, or solid non-metallic element. In exemplary embodiments, the impermeable substrate may be selected from the group consisting of aluminum, brass, and glass.

In other embodiments, the impermeable substrate may include a base metal and noble metal plating. Base metals are metals that corrode or oxidize in moist air. Examples of base metals may include iron, nickel, lead, tin, and zinc. Under some conditions, copper may act as a base metal. Noble metals, unlike most base metals, are metals resistant to corrosion and oxidation in moist air. Noble metals tend to be precious, often due to their rarity in the Earth's crust. The metal may be in the form of a foil. In other embodiments, the impermeable substrate may include stainless steel. In still other embodiments, the impermeable substrate may be a material that can be soldered to make a glass-metal or metal-metal seal or junction.

The impermeable substrate may have a thickness that is large enough to maintain the impermeability of the substrate against the analyte during testing or under testing conditions. Alternatively, the thickness may be selected to allow handling by the user, but not so thick as to render the permeation standard impractical by its thickness or its weight. For example, the impermeable substrate may have a thickness from about 0.2 mm to about 20 cm.

(b) Orifice

As shown in FIGS. 1A and 1B, the orifice 120 may be a hole, pinhole, aperture, or opening disposed in the impermeable substrate 110 and traversing through the thickness of the substrate 110 from one face to the opposite face. The orifice 120 may have any suitable cross-sectional shape, such as circular, square, rectangular, or polygonal. The diameter of the orifice 120 may range from about 100 nm to about 10 mm. Further, as shown in FIG. 1C, the orifice 120 may form a maze-shaped channel that traverses through the thickness of the substrate 110 from one face to the opposite face. As shown in FIG. 1D, the orifice 120 may occupy a portion of an opening 160 within the substrate 110. The orifice 120 is filled with a permeable material 130, such as a polymer. The permeable material 130 slows the diffusion of the analyte through the orifice 120.

(i) Permeable Material

The permeation standards disclosed herein include a permeable material. In some embodiments, the permeable material may include a mesoporous material, a gel, or another non-impermeable material. In some embodiments, the permeable material includes a polymer. Generally the polymer may be hydrophobic; that is, the polymer may have a low solubility of water, or may have a tendency not to absorb water from the environment. The polymer may adhere to the impermeable substrate or the capillary, thus withstanding the rigors of use.

The polymer may have known or determinable permeation properties, such as Fickian diffusivity. As used herein, "Fickian" refers to materials that follow Fick's laws of diffusion. Fick's first law relates the diffusive flux to the concentration under the assumption of steady state, postulating that the flux moves from regions of high concentration to regions of low concentration, with a magnitude proportional to the concentration gradient. Fick's second law predicts how diffusion causes the concentration of an analyte to change with time and can be derived from Fick's first law and the mass conservation absent any chemical reactions.

Many polymers are suitable for use as a permeable material in the permeation standards disclosed herein. Exemplary polymers include, but are not limited to, polyimide, silicone, and polyolefin. In some embodiments, the permeable material may include a non-volatile liquid, such as silicone oil. In this case, plugs of another permeable material may be used to prevent the silicone oil from leaking out from the substrate. In other embodiments, the permeable material may include a mixed material providing a percolation effect. Examples of mixed materials include polymers having a heterogeneous element, such as silica. In another exemplary embodiment, the permeable material includes a siloxane and silica, such as PDMS and microcrystalline silicon dioxide.

(ii) Capillary

In some embodiments, a capillary may be inserted into the substrate and at least partially filled with the permeable material. For example, as shown in FIGS. 2A and 2B, a capillary 240 filled with a permeable material 230 is embedded into the substrate 210 so that diffusion of the analyte occurs through the capillary 240. The capillary 240 may be held in place via a sealing material 260 or 270. The capillary 240 may have any appropriate shape, such as cylindrical, rectangular, or any other geometrical shape. The cross-sectional area of the capillary 240 through which the analyte travels is determined by the inner diameter of the capillary 240.

The capillary 240 may include the same material as the substrate 210. For example, the substrate 210 and the capillary 240 may both include glass or metal. As shown in FIGS. 2A and 2B, the capillary 240 need not have the same length as the thickness of the substrate 210. Rather, the length of the capillary 240 may be selected independently from the thickness of the substrate 210. The capillary 240 may have any suitable inner diameter, such as from about 1 µm to about 10 mm.

Alternatively, as shown in FIG. 2C, the capillary 240 may be filled with an impermeable material 290 and inserted within a permeable material 280 filling an orifice 220. In this example, the effective cross-sectional area of the permeable material 280 is reduced by the capillary 240. The impermeable material 290 may be the same as the impermeable material of the substrate 210, or may be different from the impermeable material of the substrate 210. Further, the impermeable material 290 and the capillary 240 may be made of the same material, such that the combination of the impermeable material 290 and the capillary 240 forms a solid rod, or they may be made of different materials.

(iii) Transmission Rate

By adjusting the geometry of the orifice, the geometry of the capillary, and/or the permeability of the filler material to the analyte, the transmission rate of an analyte through the permeation standard may be adjusted to any suitable value. For example, the transmission rate for water vapor (WVTR) may be adjusted to between approximately $10^{-3}$ g/m²/day and approximately $10^{-10}$ g/m²/day. The transmission rates for other analytes may be adjusted to other suitable values, and may be measured in other units. For example, the transmission rate of oxygen may be measured in ml/(m² day) or ml/(m²·atm·day), and the transmission rate of helium may be measured in 1/m²/day. It is possible to convert these transmission rates to different units, such as g/m²/day.

For a permeation standard having a single orifice filled with a permeable material, the transmission rate $TR_{standard}$ (T, PP, analyte) through the permeation standard for a specific analyte is given by the following:

$$TR_{standard}(T, PP, analyte) = \left(\frac{A}{L}\right) * TR_{permeable\_material}(T, PP, analyte) \quad (1)$$

where A is the cross-sectional area of the orifice, L is the length of the orifice, and $TR_{permeable\_material}$(T, PP, analyte) is the known transmission rate of the permeable material for the analyte as a function of the partial pressure PP and the temperature T. As discussed above, the orifice is defined as the volume within the impermeable substrate that is filled with the permeable material. Equation (1) may be modified to account for multiple orifices with various geometries, such as those shown in FIGS. 1A-1D and 2C.

If a capillary is inserted into the orifice and at least partially filled with the permeable material, such as shown in FIGS. 2A and 2B, the variables in Equation (1) are redefined such that A is the cross-sectional area of the capillary and L is the length of the filled portion of the capillary. The cross-sectional area of the capillary is defined by the inner diameter of the capillary.

Table 1 below shows projected WVTR values for a permeation standard having a glass capillary soldered into a brass substrate. This table illustrates how to vary the WVTR levels by changing the cross-sectional area of the capillary. In this example, the capillary has a length of 9.5 mm and is completely filled with PDMS. The WVTR for a capillary having a cross-sectional area of 0.50265 mm² was measured to have a value of 7.8±2.8×10⁻⁴ g/m²/day at a temperature of 45° C. and a relative humidity of 85%, which is within the error range of the predicted value of 6.6×10⁻⁴ g/m²/day under these conditions, as shown in Table 1. From this single measured data point, one can predict what the temperature-dependent WVTR would be, for instance at 5° C. and 85° C., since the PDMS demonstrates Fickian behavior.

TABLE 1

| Area | WVTR (5° C.) | WVTR (45° C.) | WVTR (85° C.) |
| --- | --- | --- | --- |
| 4.90873 | 7.81E-04 | 6.43E-03 | 1.10E-03 |
| 0.70882 | 1.13E-04 | 9.28E-04 | 5.40E-03 |
| 0.50265 | 8.00E-05 | 6.58E-04 | 3.83E-03 |
| 0.26148 | 4.16E-05 | 3.40E-04 | 1.99E-03 |
| 0.04119 | 6.55E-06 | 5.39E-05 | 3.14E-04 |
| 0.00454 | 7.22E-07 | 5.94E-06 | 3.46E-05 |
| 0.00196 | 3.12E-07 | 2.57E-06 | 1.50E-05 |
| 0.00049 | 7.81E-08 | 6.43E-07 | 3.74E-06 |

As another example, Table 2 below shows projected WVTR values for a permeation standard having a cylindrical capillary soldered into a substrate. In this example, the capillary has a length of 10 mm and is filled with PDMS. The cross-sectional area of the capillary is determined by its inner diameter. The inner diameter of the cylindircal capillary is given in mm, and the WVTR values are given in g/m²/day.

TABLE 2

| Diameter | WVTR |
| --- | --- |
| 0.001 | 1.50E-09 |
| 0.01 | 1.50E-07 |
| 0.1 | 1.50E-05 |
| 1 | 1.50E-03 |
| 10 | 1.50E-01 |

The transmission rate of the permeation standard may also be tuned based on the number of orifices and/or capillaries. For example, the permeation standard 100 shown in FIG. 1B has a first orifice 130 and a second orifice 150. If these two orifices have the same geometry and are filled with the same material, the WVTR through the permeation standard 100 shown in FIG. 1B should be double the WVTR through the permeation standard 100 shown in FIG. 1A, which only includes the first orifice 130.

(iv) Multilayer Structures

In some embodiments, the permeation standard may further include a second substrate that is impermeable to the analyte. For example, as shown in FIG. 3, a second orifice 325 is disposed in a second substrate 315, and a second permeable material fills the second orifice 325. The first substrate 310 and the second substrate 315 may be disposed to form a space such that the first orifice 320 and the second orifice 325 do not align. A third permeable material 330 may fill the space between the first substrate 310 and the second substrate 315. In particular embodiments, the first, second, and third permeable materials may include the same polymer. The analyte may travel through the first orifice 320 to the second orifice 325 via the third permeable material 330.

The arrangement shown in FIG. 3 elongates the diffusion path of an analyte from one side of the permeation standard 300 to the other side of the permeation standard 300. Such a configuration may decrease the transmission rate of the permeation standard 300, particularly if the first, second, and third permeable materials are different. The vertical distance between the first substrate 310 and the second substrate 315 may be much smaller than the horizontal distance between the first orifice 320 and the second orifice 325. Such a permeation standard may be fabricated and used to generate lag or breakthrough standards, effectively generating a tortuous path that the analyte must traverse before measurement by an instrument. In other embodiments, the permeation standard may include more than two substrates and more than one permeable material layer. The permeation standard may include any suitable n number of impermeable substrates and n−1 permeable material layers between each pair of substrates, wherein n is any integer larger than 1.

(II) Methods for Making a Permeation Standard

A method for making a permeation standard includes forming an orifice in a substrate that is impermeable to an analyte. The orifice may occupy part of an opening in the substrate. The orifice is then filled with a permeable material. As discussed above, the geometry of the orifice and the permeability of the filler material to the analyte may be selected to achieve a desired transmission rate of the permeation standard. For example, the transmission rate for water vapor may be selected to range between approximately $10^{-3}$ g/m²/day to $10^{-10}$ g/m²/day.

In some embodiments, the orifice may be formed by mechanically drilling, laser etching, or arc welding into the substrate. Alternatively, the orifice may be formed in the substrate by mechanical puncturing with a finite sharpened tip, an arc flash to heat or anneal through the substrate over a finite area, or laser scribing. In order to form an orifice with small features, etching of a silicon substrate may advantageously be used. The method may also include inserting a capillary filled with an impermeable material into the orifice.

In some embodiments, the method may further include forming a second orifice in a second substrate impermeable to the analyte; filling the second orifice with a second permeable material; disposing the substrate and second substrate to form a space such that the first orifice and the second orifice do not align; and filling the space between the substrate and the second substrate with a third permeable material.

Alternatively, the method may include inserting a capillary into an opening in the substrate, and sealing the capillary onto the substrate. In some embodiments, the capillary may be at least partially filled with a polymer. An impermeable or hermetic seal may be formed between the capillary and the impermeable substrate, for example solder or a metal/glass seal. In particular, the sealing step may be selected from the group consisting of soldering (e.g., indium solder), welding, forming a glass-glass seal with frits, and forming a metal-glass seal. In other embodiments, the substrate may be metallized with an easily soldered metal, such as silver. The metallization may be performed by the evaporation of a metal source or by the deposition of a metal salt, thereby allowing the use of standard solders. Adhering material may be applied such that substantially no leakage occurs, the polymer characteristics are unchanged, and the hole size is not significantly altered.

While a number of exemplary aspects and embodiments have been discussed above, those of skill in the art will recognize certain modifications, permutations, additions, and sub combinations thereof. It is therefore intended that the following appended claims and claims hereafter introduced are interpreted to include all such modifications, permutations, additions and sub-combinations as are within their true spirit and scope.

What is claimed is:

1. A permeation standard comprising:
   a first substrate that is impermeable to an analyte;
   a first orifice disposed in the first substrate; and
   a first permeable material filling the first orifice;
   wherein the first permeable material comprises a material other than a gas, and
   wherein the first orifice and the first permeable material are configured to provide a predetermined transmission rate of the analyte through the permeation standard.

2. The permeation standard of claim 1, wherein the predetermined transmission rate of the analyte through the permeation standard is determined by a geometry of the first orifice and a permeability of the first permeable material to the analyte.

3. The permeation standard of claim 2, wherein the geometry of the first orifice includes a cross-sectional area of the first orifice and a length of the first orifice.

4. The permeation standard of claim 1, wherein the analyte is water vapor and the predetermined transmission rate of the analyte through the permeation standard is less than approximately $10^{-3}$ g/m²/day.

5. The permeation standard of claim 1, wherein the first orifice has a diameter between approximately 100 nm and approximately 10 mm.

6. The permeation standard of claim 1, wherein the first substrate is selected from the group consisting of a copper-containing alloy, aluminum, a steel alloy, silicon, and glass.

7. The permeation standard of claim 1, wherein the first permeable material comprises a polymer or a composite material.

8. The permeation standard of claim 1, further comprising a capillary disposed in the first orifice, wherein the capillary is filled with an impermeable material.

9. The permeation standard of claim 1, further comprising:
   a second substrate that is impermeable to the analyte;
   a second orifice disposed in the second substrate; and
   a second permeable material filling the second orifice;

wherein the first substrate and the second substrate are disposed to form a space such that the first orifice and the second orifice do not align, and wherein a third permeable material fills the space between the first substrate and the second substrate.

10. The permeation standard of claim 9, wherein the first, second, and third permeable materials comprise the same polymer.

11. The permeation standard of claim 1, further comprising:

a second orifice disposed in the first substrate, wherein the first permeable material fills the second orifice.

12. A permeation standard comprising:
a substrate that is impermeable to an analyte;
a capillary disposed in the substrate; and
a permeable material at least partially filling the capillary;
wherein the permeable material comprises a material other than a gas, and
wherein the capillary and the permeable material are configured to provide a predetermined transmission rate of the analyte through the permeation standard.

13. The permeation standard of claim 12, wherein the predetermined transmission rate of the analyte through the permeation standard is determined by a geometry of the capillary and a permeability of the permeable material to the analyte.

14. The permeation standard of claim 13, wherein the geometry of the capillary includes a cross-sectional area of the capillary and a length of a filled portion of the capillary.

15. The permeation standard of claim 12, wherein the analyte is water vapor and the predetermined transmission rate of the analyte through the permeation standard is less than approximately $10^{-3}$ g/m$^2$/day.

16. A method for making a permeation standard, the method comprising:

forming a first orifice in a first substrate that is impermeable to an analyte;
selecting a first permeable material; and
filling the first orifice with the first permeable material;
wherein the first permeable material comprises a material other than a gas, and
wherein the first orifice is formed and the first permeable material is selected to provide a predetermined transmission rate of the analyte through the permeation standard.

17. The method of claim 16, wherein the predetermined transmission rate of the analyte through the permeation standard is determined by a geometry of the first orifice and a permeability of the first permeable material to the analyte.

18. The method of claim 17, wherein the geometry of the first orifice includes a cross-sectional area of the first orifice and a length of the first orifice.

19. The method of claim 16, wherein the analyte is water vapor and the predetermined transmission rate of the analyte through the permeation standard is less than approximately $10^{-3}$ g/m$^2$/day.

20. The method of claim 16, further comprising:

forming a second orifice in a second substrate that is impermeable to the analyte;
filling the second orifice with a second permeable material;
disposing the first substrate and second substrate to form a space such that the first orifice and the second orifice do not align; and
filling the space between the first substrate and the second substrate with a third permeable material.

21. The method of claim 20, wherein the first, second, and third permeable materials comprise the same polymer.

22. The method of claim 16, further comprising:
forming a second orifice in the first substrate; and
filling the second orifice with the first permeable material.

23. A method for making a permeation standard, the method comprising:

inserting a capillary into an opening in a substrate that is impermeable to an analyte;
sealing the capillary onto the substrate;
selecting a permeable material; and
at least partially filling the capillary with the permeable material;
wherein the permeable material comprises a material other than a gas, and
wherein the capillary and the permeable material are selected to provide a predetermined transmission rate of the analyte through the permeation standard.

24. The method of claim 23, wherein the sealing is performed by soldering, welding, forming a glass-glass seal with frits, or forming a metal-glass seal.

25. The method of claim 23, wherein the predetermined transmission rate of the analyte through the permeation standard is determined by a length of a filled portion of the capillary, a cross-sectional area of the capillary, and a permeability of the permeable material to the analyte.

26. The permeation standard of claim 1, wherein the permeable material and the analyte comprise two different materials.

* * * * *